United States Patent
Cho et al.

(10) Patent No.: US 9,885,669 B2
(45) Date of Patent: Feb. 6, 2018

(54) METHOD OF INSPECTING A SUBSTRATE

(75) Inventors: Soo-Young Cho, Seoul (KR); Hee-Wook You, Anyang-si (KR); Bong-Ha Hwang, Seoul (KR); Hee-Tae Kim, Yongin-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 1035 days.

(21) Appl. No.: 13/977,499

(22) PCT Filed: Dec. 29, 2011

(86) PCT No.: PCT/KR2011/010316
§ 371 (c)(1),
(2), (4) Date: Sep. 20, 2013

(87) PCT Pub. No.: WO2012/091494
PCT Pub. Date: Jul. 5, 2012

(65) Prior Publication Data
US 2014/0009601 A1 Jan. 9, 2014

(30) Foreign Application Priority Data

Dec. 29, 2010 (KR) .................. 10-2010-0138104
Dec. 27, 2011 (KR) .................. 10-2011-0143703

(51) Int. Cl.
G01B 11/25 (2006.01)
G01B 11/06 (2006.01)
(Continued)

(52) U.S. Cl.
CPC ..... G01N 21/9501 (2013.01); G01B 11/0608 (2013.01); G01B 11/25 (2013.01); H05K 13/08 (2013.01)

(58) Field of Classification Search
None
See application file for complete search history.

(56) References Cited

U.S. PATENT DOCUMENTS 5,780,866 A * 7/1998 Yamamura ........... G01B 11/026
250/201.4
8,947,632 B2 * 2/2015 Staals .................. G03F 9/7003
355/52
(Continued)

FOREIGN PATENT DOCUMENTS

CN 1510393 7/2004
JP 11-237344 8/1999
(Continued)

OTHER PUBLICATIONS

Written Opinion of the International Searching Authority for International Application No. PCT/KR2011/010316, dated Sep. 5, 2012.
(Continued)

Primary Examiner — Kevin McInnish
(74) Attorney, Agent, or Firm — Kile Park Reed & Houtteman PLLC

(57) ABSTRACT

A method of inspecting a substrate is disclosed. The method is performed by a substrate-inspecting apparatus having at least one projecting module projecting a patterned light onto a substrate fixed on a stage and an inspecting module with a camera capturing an image, and inspecting a plurality of inspection regions of the substrate step by step. The method comprises, setting an inspection order of the inspecting regions according to a lengthwise direction of the substrate, estimating height displacement of a target inspection region by using a tendency information regarding at least one previous inspection region that is already inspected, adjusting height of the inspecting module by using the estimated height displacement of the target inspection region, and inspecting the target inspection region by using the inspecting module of which height is adjusted. Therefore, inspection time is reduced.

22 Claims, 11 Drawing Sheets

(51) Int. Cl.
*G01N 21/95* (2006.01)
*H05K 13/08* (2006.01)

(56) References Cited

U.S. PATENT DOCUMENTS

| | | | |
|---|---|---|---|
| 2003/0053676 A1* | 3/2003 | Shimoda | G01N 21/95684 |
| | | | 382/145 |
| 2009/0195772 A1 | 8/2009 | Fisher et al. | |
| 2011/0063603 A1* | 3/2011 | Nakano | G01N 21/94 |
| | | | 356/51 |

FOREIGN PATENT DOCUMENTS

| | | |
|---|---|---|
| JP | 2000-266691 | 9/2000 |
| JP | 2003-177101 | 6/2003 |
| KR | 10-2007-0019752 | 2/2007 |
| KR | 10-2010-0108877 | 10/2010 |
| KR | 10-2011-0061001 | 6/2011 |
| KR | 10-2011-0089506 | 8/2011 |

OTHER PUBLICATIONS

International Search Report for International Application No. PCT/KR2011/010316, dated Sep. 5, 2012.

\* cited by examiner

【Figure 1】
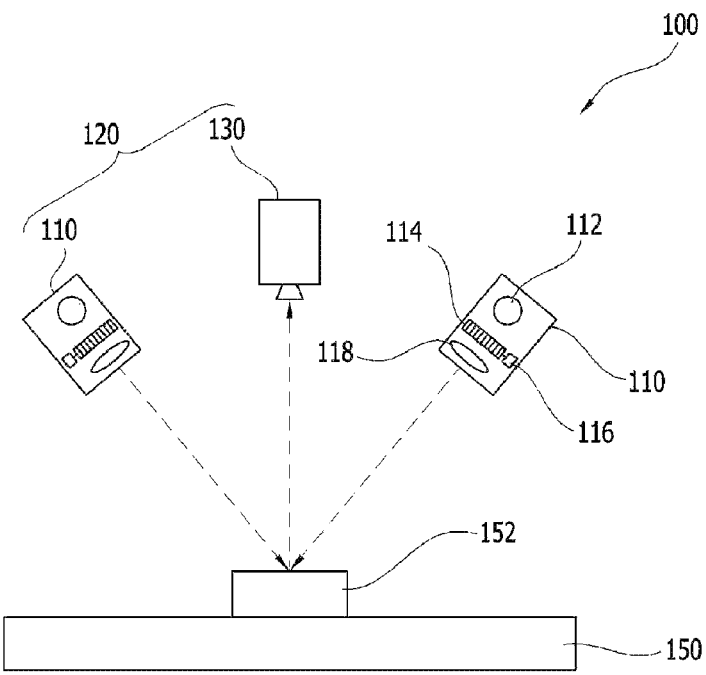
【Figure 2】
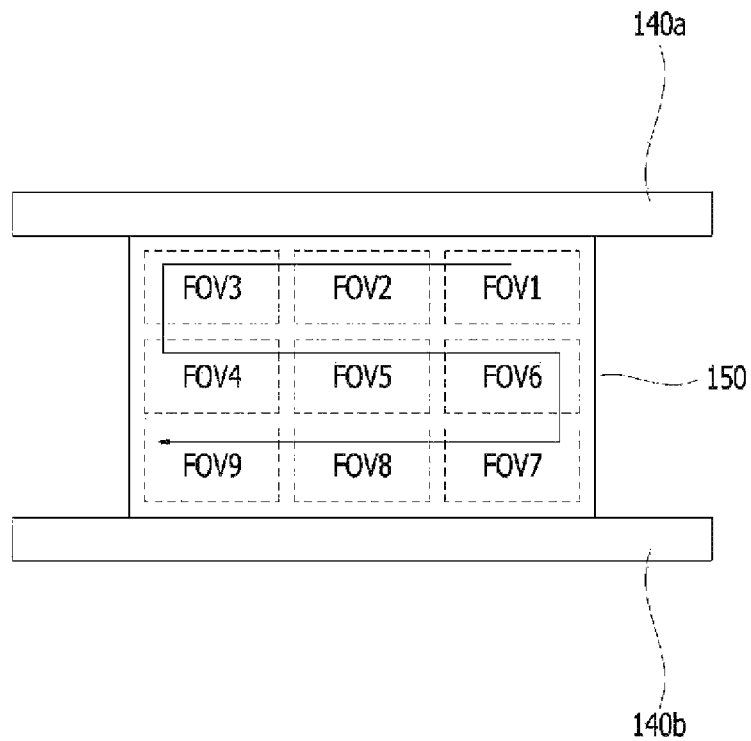

【Figure 3】
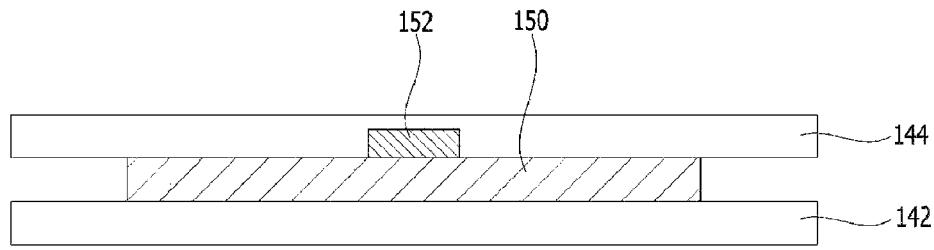
【Figure 4】
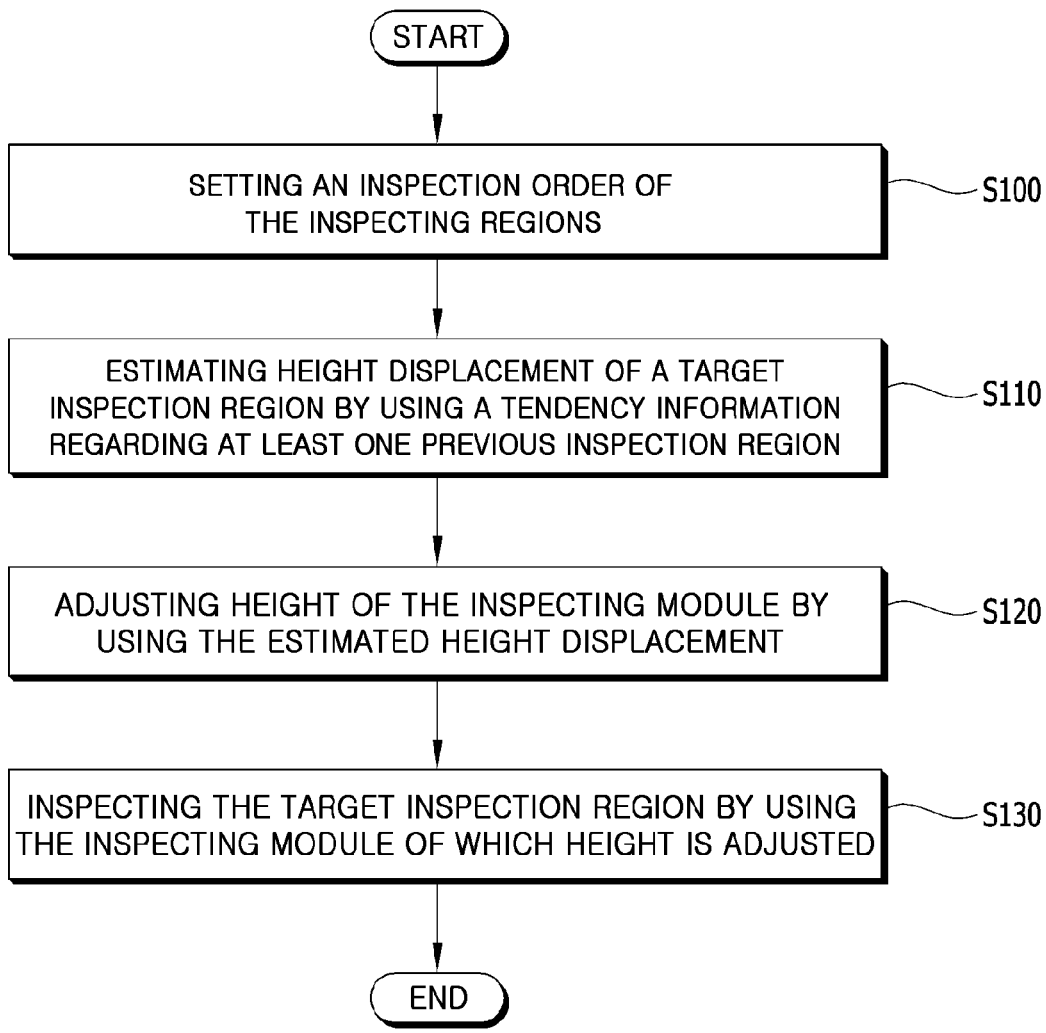

【Figure 5】
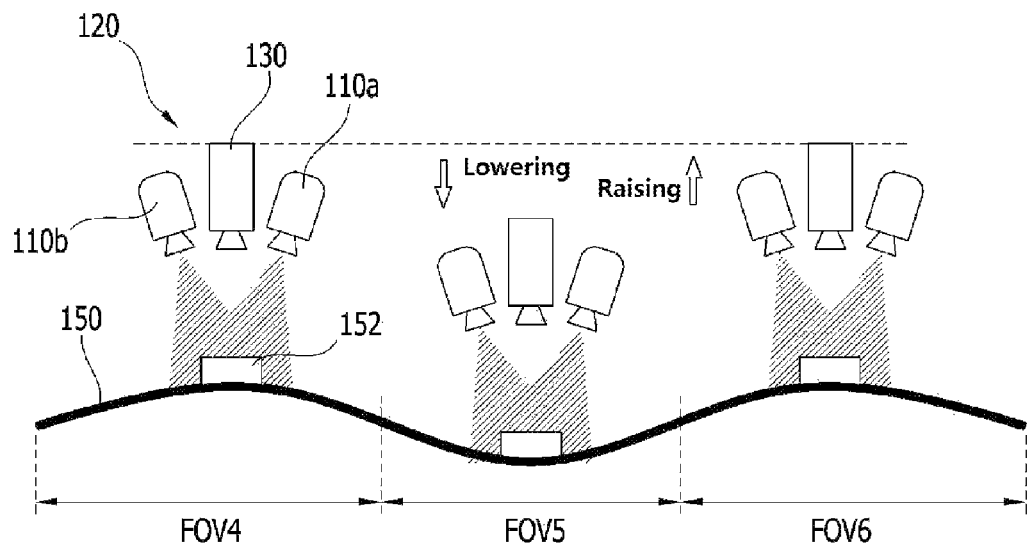
【Figure 6】
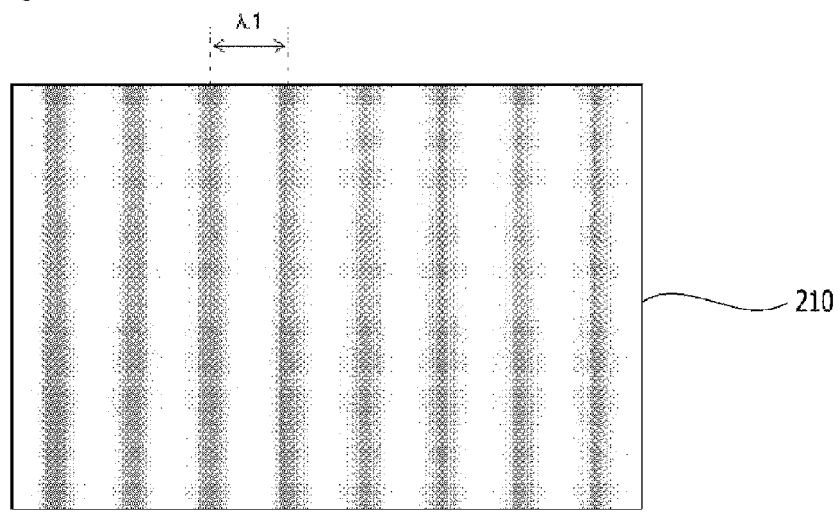

[Figure 7]
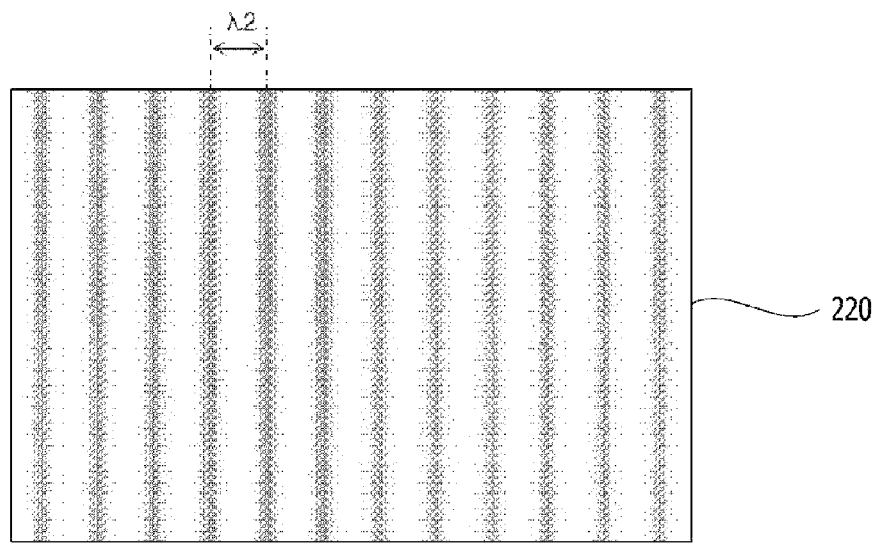
[Figure 8]
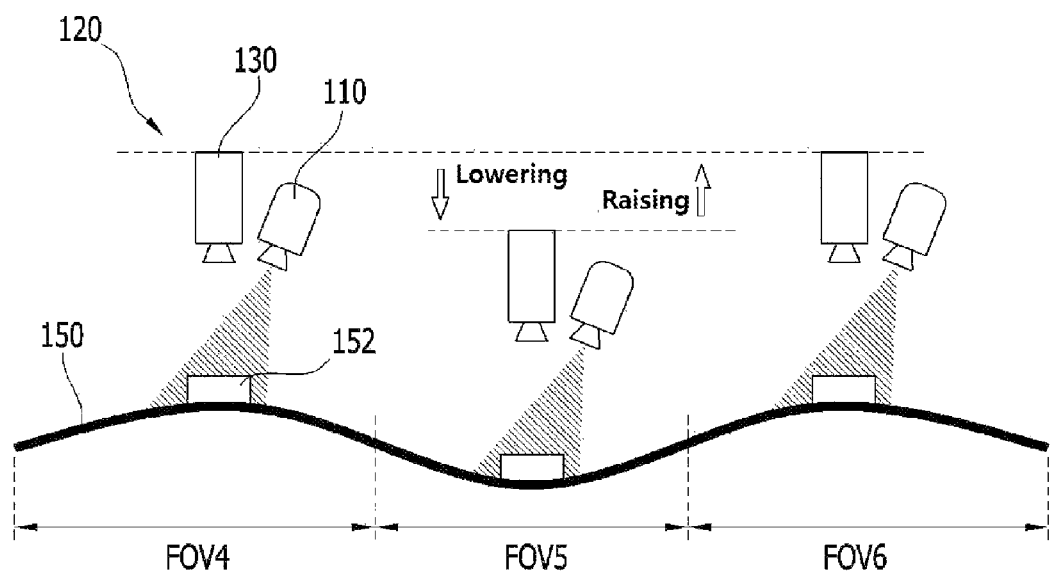

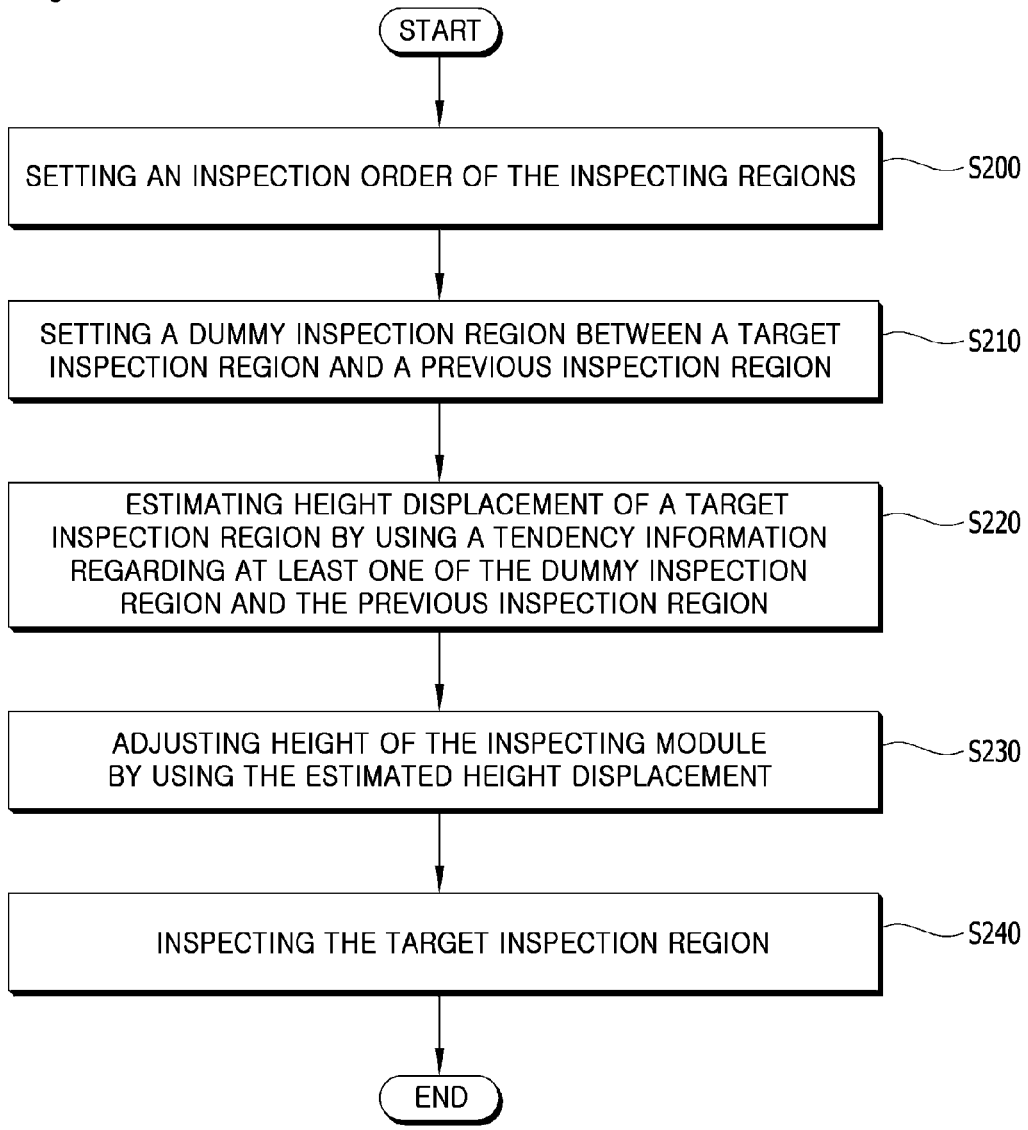

[Figure 10]
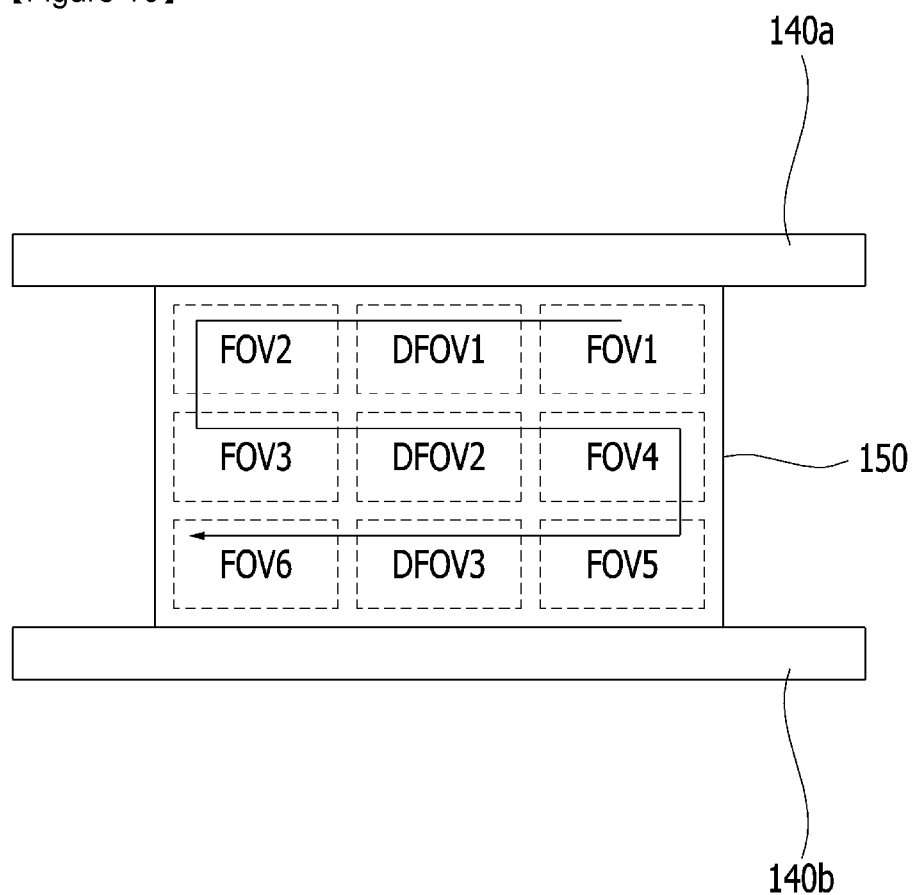

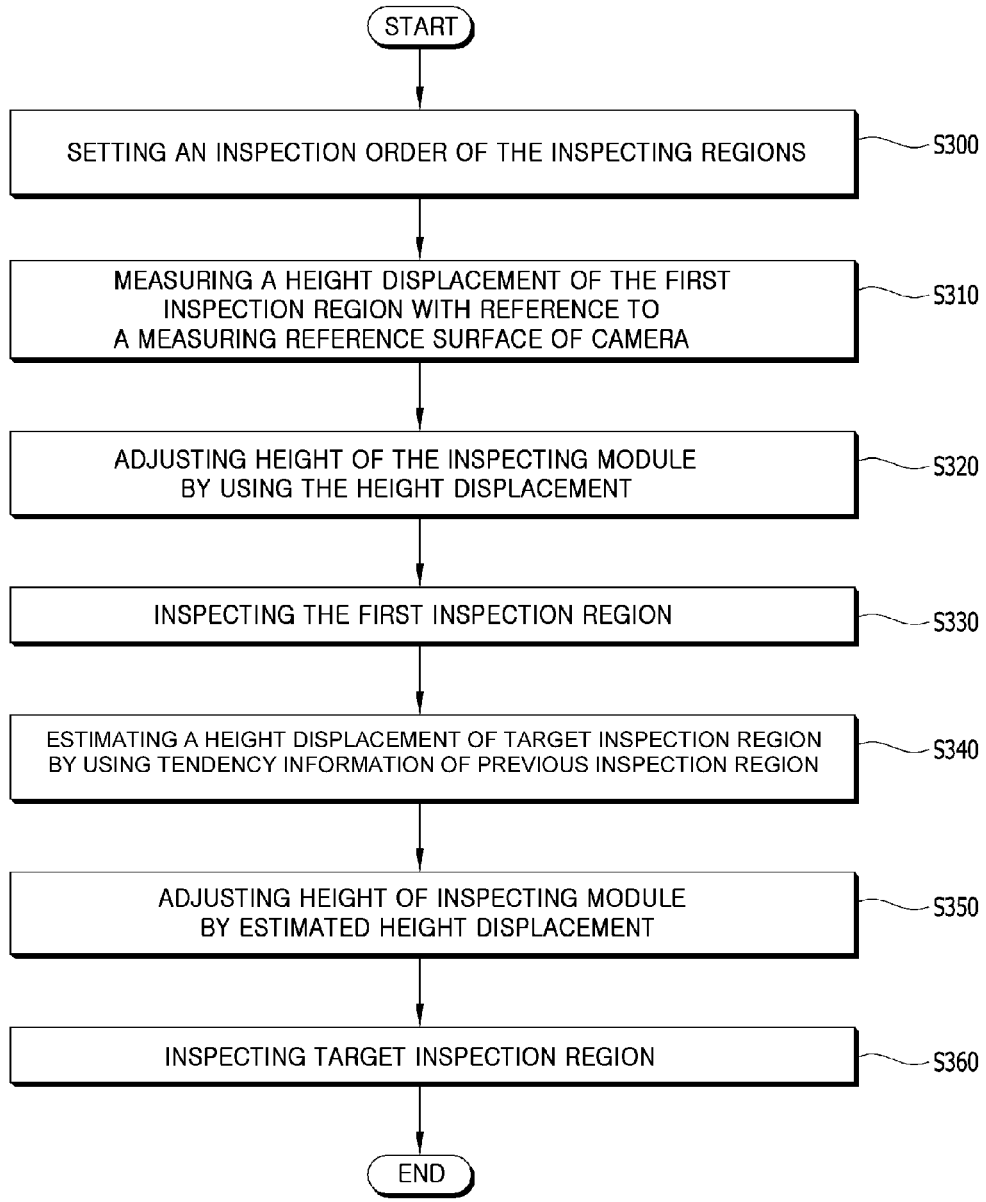

[Figure 12]
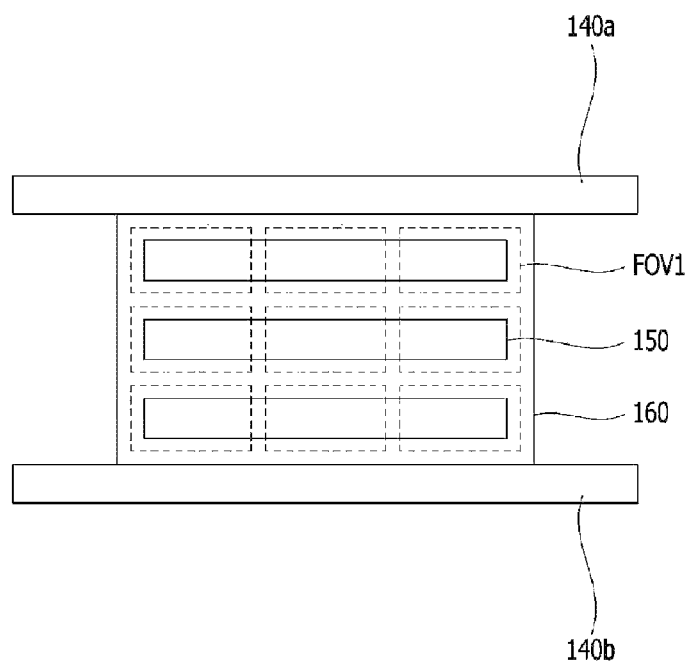
[Figure 13]
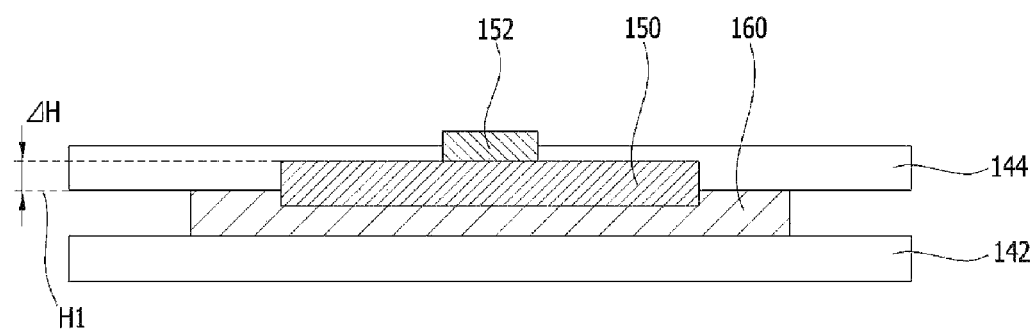

【Figure 14】
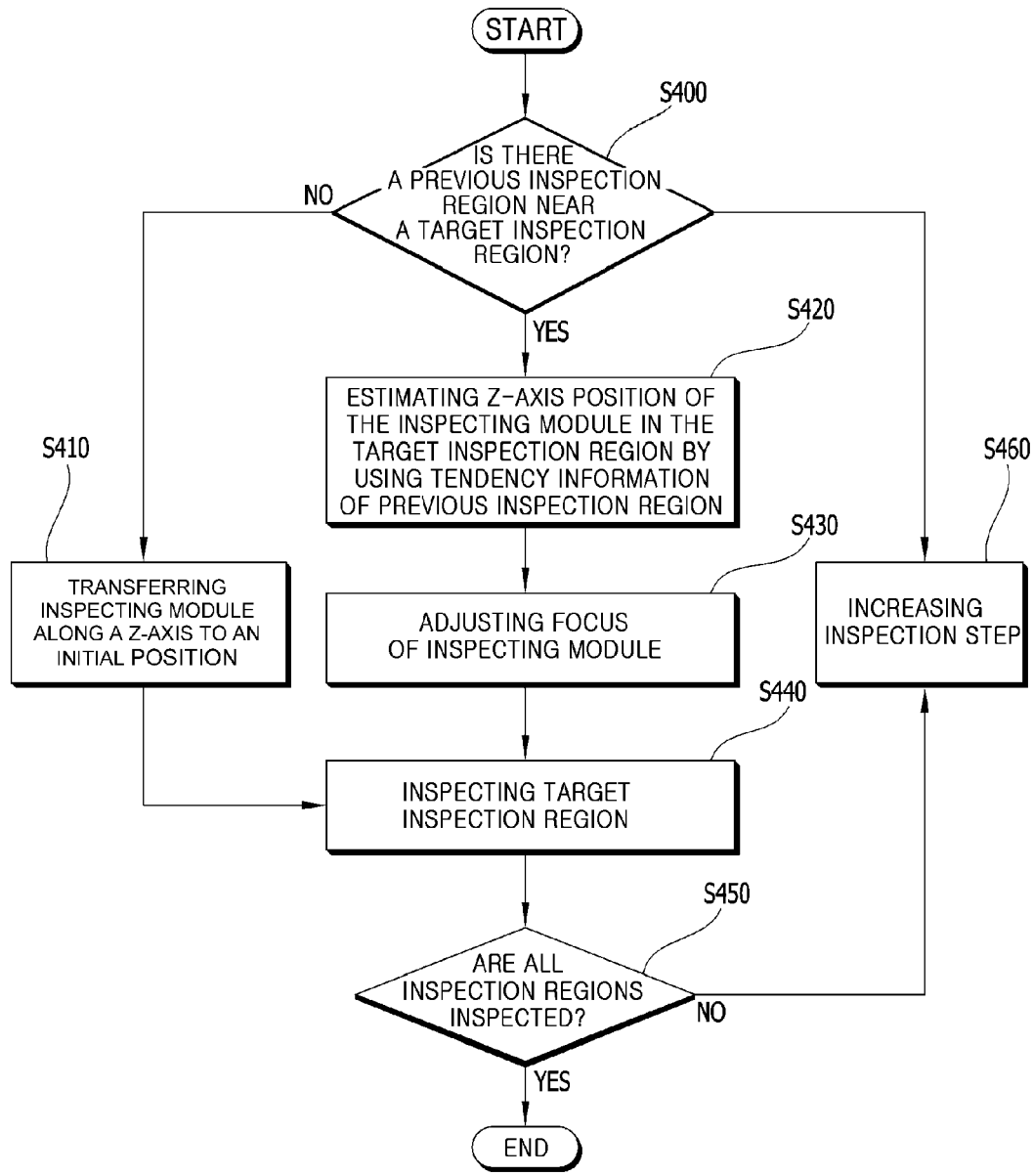

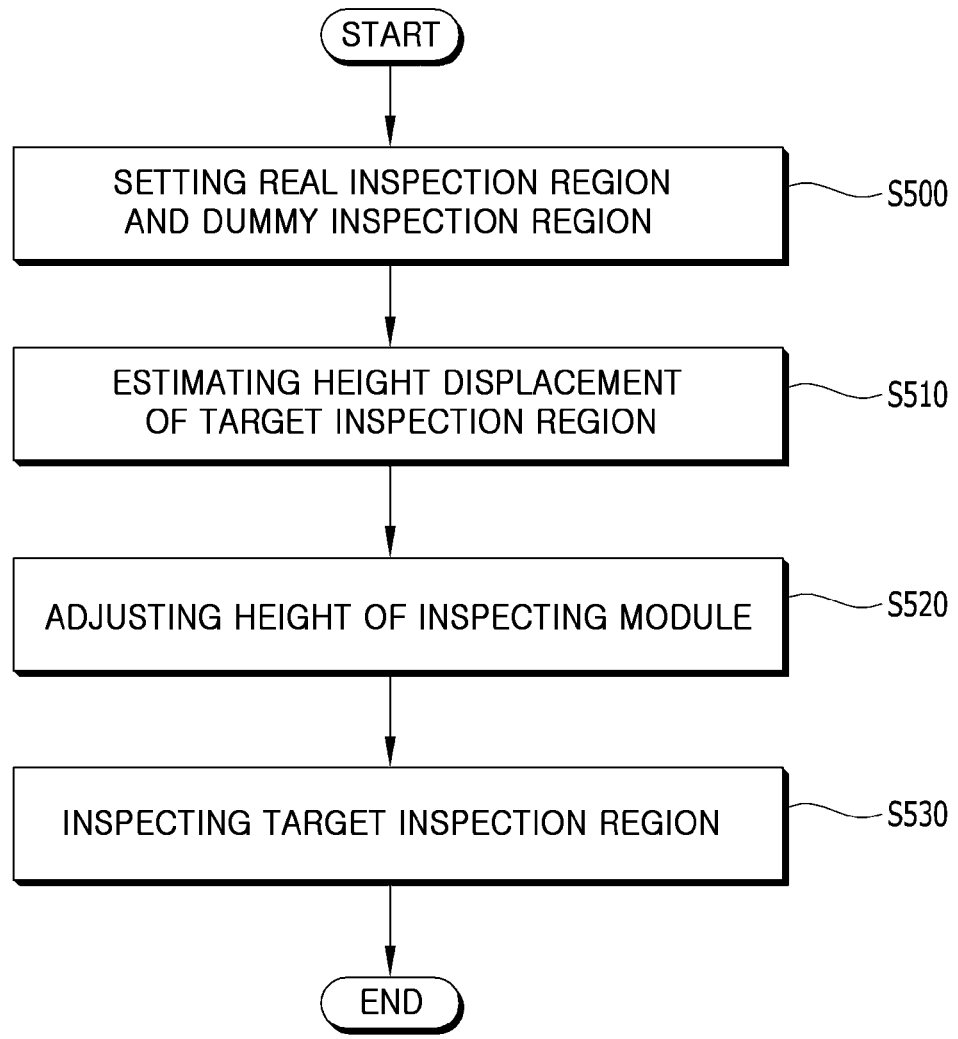
[Figure 15]

【Figure 16】
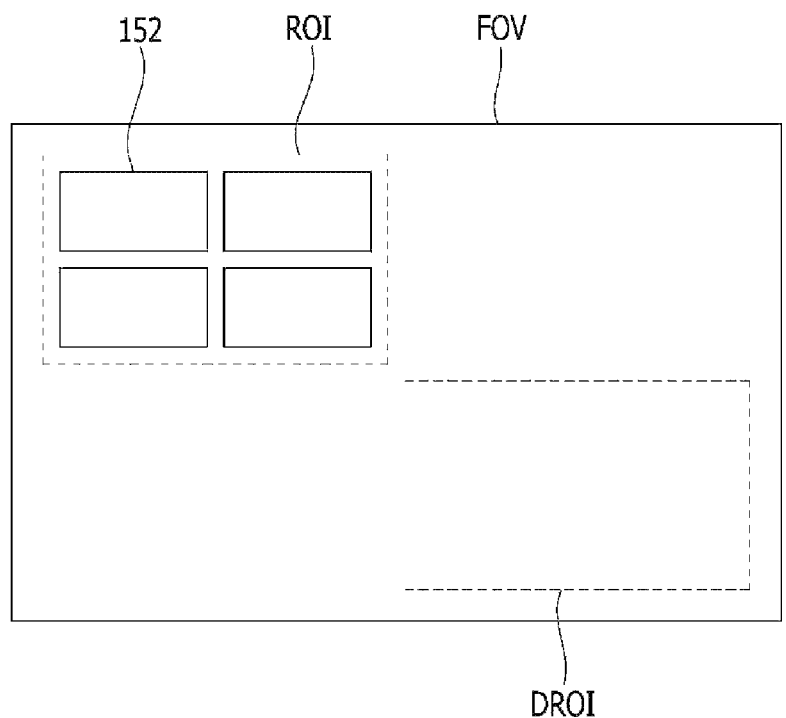

METHOD OF INSPECTING A SUBSTRATE

TECHNICAL FIELD

Exemplary embodiments of the present invention relate to a method of inspecting a substrate. More particularly, exemplary embodiments of the present invention relate to a method of inspecting a substrate, which is capable of enhancing a reliability of inspecting a status of a target object formed on a substrate.

BACKGROUND ART

In general, a target object is inspected whether the target object is properly formed before and after the target object is formed on a substrate, in order to enhance a reliability of the substrate having the target object formed thereon. For example, a solder paste formed on a substrate is inspected before an electronic device is mounted on the substrate through the solder paste, or an electronic device is inspected whether the electronic device is properly mounted on a substrate after the electronic device is mounted on the substrate through a solder paste.

Recently, a three dimensional inspecting method using a substrate-inspecting apparatus having at least one projection module and an inspecting module, is used for a precise inspection. The projection module includes a light source and a grid pattern for projecting patterned light, and the inspecting module includes a camera for capturing an image formed by the patterned light when the patterned light is reflected by a target object.

The substrate-inspecting apparatus may inspect all regions of the substrate at once. However, when the size of a substrate is greater than a field of view FOV of the camera, the substrate-inspecting apparatus may inspect a plurality of divided regions of the substrate step by step.

When the substrate is inspected by the substrate-inspecting apparatus, both end portion of the substrate is fixed and supported. Therefore, in case of a large sized substrate, the substrate may have warpage, so that there exists a height deviation among the plurality of divided regions. In general, the substrate-inspecting apparatus has a tolerance for a height deviation. Therefore, when the height deviation induced by the warpage of the substrate exceeds the tolerance, the height of a target object cannot be inspected properly.

When the substrate has a warpage to induce height deviation among inspection regions, the height deviation among the inspection region is firstly measured by a laser range finder and the height of the inspecting module is adjusted by using the height deviation. However, the above method increases inspection time.

DISCLOSURE

Technical Problem

Exemplary embodiments of the present invention provide a method of inspecting a substrate, which is capable of reducing inspection time by adjusting height of the inspecting module regarding a target inspection region to be inspected by using height tendency information of at least one previous inspection region that is already inspected.

Additionally, exemplary embodiments of the present invention provide a method of inspecting a substrate, which is capable of increasing height inspection range by using a first patterned light with a first wavelength and a second patterned light with a second wavelength that is different from the first wavelength, even when a substrate has a warpage.

Additionally, exemplary embodiments of the present invention provide a method of inspecting a substrate, which is capable of enhancing accuracy of height displacement regarding a target inspection region by setting a dummy inspection region between the target inspection region and a previous inspection region that is already inspected, when the target inspection region is widely spaced apart from the previous inspection region.

Additionally, exemplary embodiments of the present invention provide a method of inspecting a substrate, which is capable of enhancing a reliability of inspection by adjusting height of a camera by height displacement of a substrate, which is induced by a substrate transferor such as a tray or a jig, when the substrate is carried by the substrate transferor.

Additionally, exemplary embodiments of the present invention provide a method of inspecting a substrate, which is capable of enhancing a reliability of inspection by setting dummy region of interest for acquiring height tendency of an inspection region, when a region of interest ROI, in which a target object is disposed, is too much to one side in the inspection region.

Technical Solution

According to a method of inspecting a substrate of an exemplary embodiment of the present invention, a substrate-inspecting apparatus having at least one projecting module projecting a patterned light onto a substrate fixed on a stage and an inspecting module with a camera capturing an image, and inspecting a plurality of inspection regions of the substrate step by step is used. The method comprises, setting an inspection order of the inspecting regions according to a lengthwise direction of the substrate, estimating height displacement of a target inspection region by using a tendency information regarding at least one previous inspection region that is already inspected, adjusting height of the inspecting module by using the estimated height displacement of the target inspection region, and inspecting the target inspection region by using the inspecting module of which height is adjusted.

The height displacement of a target inspection region may be estimated by using the tendency information of at least one previous inspection region that is already inspected through an extrapolation method. For example, the height displacement of a target inspection region may be estimated by using height information of at least two previous inspection regions existing in a same row along the lengthwise direction. For another example, the height displacement of a target inspection region may be estimated by using height information of at least three previous inspection regions existing in a same row and a previous row along the lengthwise direction.

The tendency information regarding the previous inspection region may correspond to a surface equation obtained by using height information of at least one region of interest ROI in the previous inspection region.

The height of the inspecting module may be adjusted before the inspecting module is transferred to the target inspection region, after the inspecting module is transferred to the target inspection region, or during the inspecting module is transferred to the target inspection region.

The height of the inspecting module may be adjusted based on height displacements of a center of the target inspection region and the previous inspection region.

The projecting module may include at least one first projecting module projecting a first patterned light with a first wavelength, and at least one second projecting module projecting a second patterned light with a second wavelength that is different from the first wavelength. Alternatively, the projecting module may project a first patterned light with a first wavelength and a second patterned light with a second wavelength different from the first wavelength in sequence.

According to a method of inspecting a substrate of another exemplary embodiment of the present invention, a substrate-inspecting apparatus having at least one projecting module projecting a patterned light onto a substrate fixed on a stage and an inspecting module with a camera capturing an image, and inspecting a plurality of inspection regions of the substrate step by step is used. The method includes setting an inspection order of the inspecting regions, setting at least one dummy inspection region between a target inspection region and a previous inspection region that is already inspected, estimating height displacement of a target inspection region by using a tendency information regarding at least one of the dummy inspection region and the previous inspection region, adjusting height of the inspecting module by using the estimated height displacement of the target inspection region, and inspecting the target inspection region by using the inspecting module of which height is adjusted.

The tendency information regarding the dummy inspection region and the previous inspection region may correspond to a surface equation obtained by using height information of at least one region of interest ROI in the dummy inspection region and the previous inspection region, respectively.

The projecting module may include at least one first projecting module projecting a first patterned light with a first wavelength, and at least one second projecting module projecting a second patterned light with a second wavelength that is different from the first wavelength. Alternatively, the projecting module may project a first patterned light with a first wavelength and a second patterned light with a second wavelength different from the first wavelength in sequence.

According to a method of inspecting a substrate of still another exemplary embodiment of the present invention, a substrate-inspecting apparatus having at least one projecting module projecting a patterned light onto a substrate mounted on a substrate transferor and fixed to a stage together with the substrate transferor and an inspecting module with a camera capturing an image, and inspecting a plurality of inspection regions of the substrate step by step, is used. The method includes, setting an inspection order of the inspecting regions according to a lengthwise direction of the substrate, measuring a first inspection region to acquire a height displacement of the first inspection region with reference to a measuring reference surface of the inspecting module, which is already set, adjusting height of the inspecting module by using the height displacement, and inspecting the first inspection region by using the inspecting module of which height is adjusted.

The method may further include estimating height displacement of a target inspection region to be inspected next by using a tendency information regarding at least one previous inspection region that is already inspected, adjusting height of the inspecting module by using the estimated height displacement of the target inspection region, and inspecting the target inspection region by using the inspecting module of which height is adjusted.

The tendency information regarding the previous inspection region may correspond to a surface equation obtained by using height information of at least one region of interest ROI in the previous inspection region.

The projecting module may include at least one first projecting module projecting a first patterned light with a first wavelength, and at least one second projecting module projecting a second patterned light with a second wavelength that is different from the first wavelength. Alternatively, the projecting module may project a first patterned light with a first wavelength and a second patterned light with a second wavelength different from the first wavelength in sequence.

According to a method of inspecting a substrate of still another exemplary embodiment of the present invention, a substrate-inspecting apparatus having at least one projecting module projecting a patterned light onto a substrate fixed on a stage and an inspecting module with a camera capturing an image, and inspecting a plurality of inspection regions of the substrate step by step, is used. The method includes checking if there is at least one previous inspection region that is already inspected near a target inspection region to be inspected, transferring the inspecting module to an initial position along a z-axis to adjust a focus, when there is not the previous inspection region, estimating an z-axis position of the inspecting module in the target inspection region by using tendency information of the previous inspection region, when there is the previous inspection region, transferring the inspecting module to the estimated z-axis position along a z-axis to adjust focus, and inspecting the target inspection region by using the inspecting module of which focus is adjusted.

The projecting module may include at least one first projecting module projecting a first patterned light with a first wavelength, and at least one second projecting module projecting a second patterned light with a second wavelength that is different from the first wavelength. Alternatively, the projecting module may project a first patterned light with a first wavelength and a second patterned light with a second wavelength different from the first wavelength in sequence.

According to a method of inspecting a substrate of still another exemplary embodiment of the present invention, a substrate-inspecting apparatus having at least one projecting module projecting a patterned light onto a substrate fixed on a stage and an inspecting module with a camera capturing an image, and inspecting a plurality of inspection regions of the substrate step by step, is used. The method includes setting a dummy region of interest DROI for acquiring height tendency of a target inspection region on which a target object is formed, estimating height displacement of a next inspection region by using the height tendency obtained by at least one of the target region of interest and the dummy region of interest, adjusting height of the inspecting module based on the estimated height displacement, and inspecting the next inspection region by using the inspecting module of which height is adjusted.

The tendency information may correspond to a surface equation obtained by using height information of at least one of the target region of interest on which the target object is formed and the dummy region of interest.

The dummy region of interest may be set by a hand of an operator.

Alternatively, the dummy region of interest may be automatically set based on a position of the target region of interest. In detail, the dummy region of interest may be automatically set by checking a position of the target region of interest in the inspection region, and setting the dummy region of interest as a region of interest at a greatest distance from the target region of interest.

The projecting module may include at least one first projecting module projecting a first patterned light with a first wavelength, and at least one second projecting module projecting a second patterned light with a second wavelength that is different from the first wavelength. Alternatively, the projecting module may project a first patterned light with a first wavelength and a second patterned light with a second wavelength different from the first wavelength in sequence.

Advantageous Effects

According to the method described above, the height of the inspecting module in the target inspection region is adjusted by the height tendency information of at least one previous inspection region before inspecting the target inspection region, so that inspection range of the substrate-inspecting apparatus may be increased.

Further, when the inspection order of the inspecting regions is set along the lengthwise direction of the stage, the reliability of the inspecting module may be enhanced since height displacement is relatively small.

Further, a process of measuring inspection region by a laser range finder is not required to reduce the inspection time.

Further, when the inspection of the substrate is performed by using the first patterned light and the second patterned light of which wavelengths are different from each other, the inspection range of the substrate-inspecting apparatus may be increased comparing with the case using only one patterned light so that the reliability of inspection may be enhanced even through the substrate has severe warpage.

Further, according to an exemplary embodiment of the present invention, the dummy inspection regions are set between the inspection regions when the inspection regions are widely spaced apart from each other, so that the height displacement of the target inspection region may be more precisely estimated.

Further, according to an exemplary embodiment, the z-axis height of the camera is adjusted by an amount of height displacement of the camera, which is induced by the substrate transferor such as a tray or a jig, when the substrate is transferred by the substrate transferor, so that the reliability of the inspection may be more enhanced.

Further, when the dummy region of interest DROI is used together with the target region of interest in one inspection region FOV, the height tendency of the inspection region may be more precisely estimated, so that the height displacement of the next inspection region may be more precisely estimated to enhance reliability of inspection.

DESCRIPTION OF DRAWINGS

FIG. 1 is a schematic view showing a substrate-inspecting apparatus according to an exemplary embodiment of the present invention.

FIG. 2 is a plan view showing a substrate fixed to a stage.

FIG. 3 is a side view showing a substrate fixed to a stage.

FIG. 4 is a flow chart showing a method of inspecting a substrate according to an exemplary embodiment of the present invention.

FIG. 5 is a schematic view showing a method of inspecting a substrate according to an exemplary embodiment of the present invention.

FIG. 6 and FIG. 7 are plan view showing a first patterned light and a second patterned light projected by a projecting module, respectively.

FIG. 8 is a schematic view showing a method of inspecting a substrate according to another exemplary embodiment of the present invention.

FIG. 9 is a flow chart showing a method of inspecting a substrate according to another exemplary embodiment of the present invention.

FIG. 10 is a plan view showing a substrate fixed to a stage according to another exemplary embodiment of the present invention.

FIG. 11 is a flow chart showing a method of inspecting a substrate according to still another exemplary embodiment of the present invention.

FIG. 12 is a plan view showing a substrate fixed to a stage according to still another exemplary embodiment of the present invention.

FIG. 13 is a side view showing a substrate fixed to a stage according to still another exemplary embodiment of the present invention.

FIG. 14 is a flow chart showing a method of inspecting a substrate according to still another exemplary embodiment of the present invention.

FIG. 15 is a flow chart showing a method of inspecting a substrate according to still another exemplary embodiment of the present invention.

FIG. 16 is a plan view showing one inspection region.

MODE FOR INVENTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For convenience, same numerals are used for identical or similar elements of an apparatus of cutting a tempered substrate and the conventional one.

Hereinafter, exemplary embodiments of the present invention will be described with reference to the accompanying drawings.

FIG. 1 is a schematic view showing a substrate-inspecting apparatus according to an exemplary embodiment of the present invention, FIG. 2 is a plan view showing a substrate fixed to a stage, and FIG. 3 is a side view showing a substrate fixed to a stage.

Referring to FIG. 1, FIG. 2 and FIG. 3, a substrate-inspecting apparatus 100 according to an exemplary embodiment of the present invention includes at least one projecting module 110 projecting a patterned light onto a substrate 150 having a target object 152 formed thereon, and an inspecting module 120 having a camera 130 capturing an image of the substrate 150. Additionally, the substrate-inspecting apparatus 100 includes a stage 140 supporting and fixing the substrate 150 having the target object 152 formed thereon.

The projecting module 110 projects a patterned light onto the target object 152 formed on the substrate 150 in order to measure three dimensional image of the target object 152. For example, the projecting module 110 includes a light source 112 generating light, a grid pattern 114 converting the light generated by the light source 112 into a pattered light, a grid pattern transferor 116 transferring the grid pattern by pitch, and a projecting lens 118 projecting the patterned light to the target object 152. The grid pattern 114 may be transferred by amount of $2\pi/N$ (N is a natural number) for a phase shift of the patterned light through the grid pattern transferor 116 such as a piezo actuator (PZT). The substrate-inspecting apparatus 100 may include a plurality of the projecting modules 110 having the above mentioned structure. In this case, the projecting modules 110 may be disposed along a circumference with respect to the camera 130. The projecting modules 110 are slantly installed with respect to the substrate 150 so that the projecting modules 110 project the patterned light along many directions. However, the substrate-inspecting apparatus 100 may include only one projecting module 110.

The camera 130 captures an image of the substrate 150 when the projecting module 110 projects the patterned light. For example, the camera 130 may be disposed over the substrate 150. A CCD camera or CMOS camera may be adopted as the camera 130.

The stage 140 supports and fixes the substrate 150. For example, the stage 140 supports and fixes both ends of the substrate 150. For this, the stage 140 may include a first stage 140a supporting and fixing a first end of the substrate 150 and a second stage 140b supporting and fixing a second end of the substrate 150. Further, the first and second stages 140a and 140b may respectively include a lower stage 142 making contact with a lower surface of the substrate 150, and an upper stage 144 making contact with an upper surface of the substrate 150. Therefore, when the substrate 150 is loaded between the lower stage 142 and the upper stage 144, a distance between the lower stage 142 and the upper stage 144 are reduced to fix the substrate 150. For example, the lower stage 142 moves upward to fix the substrate 150.

The substrate-inspecting apparatus 100 with the above-mentioned structure projects patterned light onto the substrate 150 fixed to the stage 140 through the projecting module 110, and captures an image reflected by the substrate 150 through the camera 130 to inspect three dimensional shape of the target object 152 on the substrate 150. For example, the substrate 150 may be a printed circuit board (PCB) having a wiring pattern and a pad, and the target object 152 may be a solder disposed on the substrate 150 or an electronic device mounted on the substrate 150.

When the substrate 150 is larger than one field of view of camera 130 in size, the substrate 150 is divided into a plurality of inspection region corresponding to the field, the substrate-inspecting apparatus 100 captures an image of the inspection region step by step. That is, as shown in FIG. 2, the substrate 150 is divided into a plurality of inspection regions (or Field Of View: FOV), and the inspecting module 120 inspects the inspection regions FOV, moving in order of inspection, so that the all area of the substrate 150 may be inspected. Therefore, it is preferably that the each of the inspection regions FOV has substantially the same size of field of view of the camera 130. Alternatively, each of the inspection regions FOV may have small size than the field of view of the cameral 30, which can be captured by the camera 130.

On the other hand, the substrate 150 may have a warpage when the substrate 150 has a large size or the substrate 150 has an electronic device mounted thereon, so that the substrate 150 may has a different height. That is, the substrate 150 may have different geographical features among the inspection regions FOV. Therefore, in order to enhance reliability of inspection, it is required to adjust focus of camera 130 of the substrate-inspecting apparatus 100 according to the inspection regions FOV. In this case the focus of the camera 130 may be adjusted by moving the inspecting module 120 along a z-axis.

Hereinafter, a method of inspecting a substrate having the plurality of inspection regions and being fixed by the stage 140 by using the inspecting module 120, will be explained in detail.

FIG. 4 is a flow chart showing a method of inspecting a substrate according to an exemplary embodiment of the present invention, and FIG. 5 is a schematic view showing a method of inspecting a substrate according to an exemplary embodiment of the present invention.

Referring to FIG. 2, FIG. 4 and FIG. 5, in inspecting the substrate 150 having the plurality of inspection regions FOV which are divided, an inspection order for the inspection regions FOV are set (step S100). In this case, the inspection order may be set along a lengthwise direction of the stage 140. For example, as shown in FIG. 2, when the substrate 150 is divided into nine inspection regions FOV1~FOV9, the inspection order is set such that an inspection region adjacent to the stage 140 is set as a first inspection region FOV1, and inspection order of other inspection regions are set along a lengthwise direction from the second inspection region FOV2 through FOV 9 (FOV1->FOV2->FOV3->FOV4->FOV5->FOV6->FOV7->FOV8->FOV9).

When inspection regions which are adjacent to the stage 140 are set as the first inspection region FOV1 with no tendency information, and the second inspection region FOV2 with a little tendency information along the lengthwise direction, the warpage of the substrate 150 make relatively a little influence since the inspection regions which are adjacent to stage 140 are fixed to the stage 140.

Then, in inspecting the plurality of inspection regions FOV, height displacement of a target inspection region is estimated by using a tendency information regarding at least one previous inspection region that is already inspected (step S110). That is, for inspecting the plurality of inspection regions FOV in order, the height displacement of the target inspection region that is to be inspected is estimated by using the tendency information regarding at least one previous inspection regions already inspected. In detail, the height displacement of the target inspection region is estimated by using the tendency information of at least one previous inspection region that is already inspected through an extrapolation method. On the other hand, the height displacement of the target inspection region may be estimated by using both of an extrapolation method and an interpolation method.

For example, when the target inspection region is the fifth inspection region FOV5 in FIG. 2, the previous inspection regions may correspond to the first, the second, the third and the fourth inspections regions FOV1, FOV2, FOV3 and FOV4. Therefore, the geographical features of the fifth inspection region FOV5 is estimated by using the tendency information of the first through fourth inspection regions FOV1, FOV2, FOV3 and FOV4 through the extrapolation method, and then the z-axis position of the inspecting module 120 is calculated by the geographical features of the fifth inspection region FOV5. In this case, all geographical features of the first, second, third and fourth inspection regions FOV1, FOV2, FOV3 and FOV4 may be used, but at least one of the geographical features of the first, second, third and fourth inspection regions FOV1, FOV2, FOV3 and FOV4 may be used. That is, a step of selecting previous inspection regions for estimating the geographical features of the fifth inspection region FOV5 may be performed among the first, second, third and fourth inspection regions FOV1, FOV2, FOV3 and FOV4, before estimating the geographical feature of the fifth inspection region FOV5.

For an exemplary embodiment, when the previous inspection region FOV that is already inspected and the target inspection region FOV that is to be inspected are on the same row along the lengthwise direction, the height displacement of the target inspection region FOV may be estimated by linear tendency information. That is, the height displacement of the target inspection region FOV is estimated by using tendency information of at least two of the previous inspection regions FOV on the same row along the lengthwise direction of the stage 140. For example, the height displacement of the center of the target inspection region FOV is estimated by using the height information of the centers of at least two of the previous inspection regions FOV on the same row along the lengthwise direction of the stage 140. For example, when the target inspection region FOV is the third inspection region FOV3, the height displacement of the third inspection region FOV3 is estimated by using the height tendency information of the first inspection region FOV1 and the second inspection region FOV2 that are already inspected.

For another exemplary embodiment, when the previous inspection regions FOV are on the same row and the previous row along the lengthwise direction of the stage 140, the height displacement of the target inspection region FOV is estimated by using a surface tendency information. That is, the height displacement of the target inspection region FOV is estimated by using at least three previous inspection regions on the same row and the previous row along the lengthwise direction of the stage 140. For example, the height displacement of the center of the target inspection region FOV may be estimated by using height information of the center of at least three of the previous inspection regions FOV on the same row and the previous row along the lengthwise direction of the stage 140. In this case, it is preferable to use the tendency information of the previous inspection regions FOV adjacent to the target inspection region FOV. For example, when the target inspection region FOV is the fifth inspection region FOV5, the height displacement of the fifth inspection region FOV5 is estimated by using the height tendency information of the second inspection region FOV2, the third inspection region FOV3 and the fourth inspection region FOV4 that are already inspected. When the target inspection region FOV is sixth inspection region FOV6, the height displacement of the sixth inspection region FOV6 is estimated by using the height tendency information of first inspection region FOV1, the second inspection region FOV2 and the fifth inspection region FOV5 that are adjacent to the sixth inspection region FOV6 among the previous inspection regions FOV that are already inspected.

The height tendency information of the previous inspection regions FOV, for example, may correspond to height tendency information of all regions of the previous inspection regions FOV. In this case, the height tendency information of all regions may include shape information of not only the three dimensional shape information of the target object 152 but also surface height information of the substrate 150. Alternatively, the height tendency information may correspond to height data of a portion of the region or point in the previous inspection regions FOV. For example, a surface equation of the inspection region may be obtained by using height information of at least one region of interest ROI in the previous inspection region. For example, the surface equation is obtained by using height information of at least one of the region of interest ROI, a bottom surface of the region of interest and an extended region of interest, and then height of the center or the contour obtained by the surface equation may be used as a reference data for estimating the height displacement. The surface equation of the previous inspection region FOV may be obtained by height information of at least three points.

When the number of the previous inspection region FOV is only one, the height displacement of target inspection region FOV may be estimated by height tendency information of the previous inspection region FOV.

After the height displacement of the target inspection region FOV is estimated, the height of the inspecting module 120 is adjusted based on the estimated height displacement of the target inspection region FOV (step S120). For example, adjusting the height of the inspecting module 120 may be performed based on the height displacement of the center of the target inspection region FOV. For example, when the target inspection region FOV is the fifth inspection region FOV5, the height of the center of the fifth inspection region FOV5 is compared with the height of the center of the fourth inspection region FOV4. When the height of the center of the fifth inspection region FOV5 is lower than the height of the center of the fourth inspection region FOV4, the inspecting module 120 is lowered along the z-axis direction. On the contrary, when the height of the center of the fifth inspection region FOV5 is higher than the height of the center of the fourth inspection region FOV4, the inspecting module 120 is raised along the z-axis direction. Or, the height displacement of the target inspection region may be compared with an initial z-axis height that is already set. The initial z-axis height is set based on the height of the substrate 150 fixed by the stage 140. For example, the initial z-axis height may be obtained by z-axis calibration of the inspecting module 120. The height of the inspecting module 120 may be adjusted before the inspecting module 120 is transferred to the target inspection region FOV, after the inspecting module 120 is transferred to the target inspection region FOV, or during the inspecting module 120 is transferred to the target inspection region FOV.

Then, the target inspection region FOV is inspected by using the inspecting module 120 of which height is adjusted (step S130).

According to the method described above, the height of the inspecting module 120 in the target inspection region is adjusted by the height tendency information of at least one previous inspection region before inspecting the target inspection region, so that the focus of the inspecting module 120 may be adjusted for precise inspection. Further, the inspection range of the substrate-inspecting apparatus 100 may be increased. Further, the distance between the camera 130 and the target object 152 is not exact, the inspection reliability for height is lowered and the size and the position of the target object 152 may be distorted. Therefore, when the height of the inspecting module 120 is adjusted, the above problems may be solved. Additionally, both ends of the substrate 150 loaded to the substrate-inspecting apparatus 100 are fixed by the stage 140, so that the warpage of the substrate 150 along the direction of the lengthwise direction of the substrate 150 is not severe in comparison with the warpage of the substrate along a widthwise direction that is substantially perpendicular to the lengthwise direction. Therefore, in setting the inspection order of the plurality of inspection regions, the inspection order is set along the lengthwise direction of the stage 140 with relatively small warpage, so that reliability of the height adjustment of the inspecting module 120 may be enhanced. Further, a process of measuring inspection region by a laser range finder is not required to reduce the inspection time.

On the other hand, the method of inspecting a substrate may adopt a multi-wavelength inspection method for increasing a scope of height inspection corresponding to the warpage of the substrate 150.

FIG. 6 and FIG. 7 are plan view showing a first patterned light and a second patterned light projected by a projecting module, respectively, and FIG. 8 is a schematic view showing a method of inspecting a substrate according to another exemplary embodiment of the present invention.

Referring to FIG. 5, FIG. 6 and FIG. 7, for the multi-wavelength inspection method, the projecting module 110 projects a first patterned light with a first wavelength and a second patterned light with a second wavelength different form the first wavelength in sequence. As an example of the multi-wavelength inspection method, the inspecting module 120 may include a first projecting module 110a projecting a first patterned light 210 with a first wavelength $\lambda_1$ in FIG. 6, and a second projecting module 110b projecting a second patterned light 220 with a second wavelength $\lambda_2$ in FIG. 7. A plurality of the first projecting module 110a and the second projecting module 110b may be arranged along a circumference with respect to the camera 130 by a constant distance.

Referring to FIG. 6, FIG. 7 and FIG. 8, as another example of the multi-wavelength inspection method, one projecting module 110 may project the first patterned light 210 and the second patterned light having different wavelength from each other in sequence. For example, the grid pattern 114 of the projecting module 110 may include a first region with a first grid pitch for the first patterned light 210, and a second region with a second grid pitch for the second patterned light 220 for the multi-wavelength inspection.

As described above, when the inspection of the substrate is performed by using the first patterned light 210 and the second patterned light 220 having different wavelength from each other, height inspection range may be increased comparing with the inspection of the substrate by using a patterned light with only one wavelength. In this case, the height inspection range is determined by the least common multiple of the first wavelength $\lambda_1$ and the second wavelength $\lambda_2$. Therefore, as the height inspection range increase, the substrate with a severe warpage may be within the height inspection range to enhance reliability of the height inspection.

FIG. 9 is a flow chart showing a method of inspecting a substrate according to another exemplary embodiment of the present invention, and FIG. 10 is a plan view showing a substrate fixed to a stage according to another exemplary embodiment of the present invention.

Referring to FIG. 9 and FIG. 10, in inspecting the substrate 150 having the plurality of inspection regions FOV which are divided, an inspection order for the inspection regions FOV are set (step S200). For example, it is preferable to set the inspection order of the inspection regions FOV in a zigzag shape along the lengthwise direction of the stage 140. For example, as shown in FIG. 9, when the substrate 150 is divided into six inspection regions (FOV1~FOV6), an inspection region adjacent to the stage 140 is set as the first inspection region FOV1, and the inspection order for other inspection regions are set in a zigzag shape along the lengthwise direction of the stage 140 (FOV1->FOV2->FOV3->FOV4->FOV5->FOV6).

Then, in inspecting the inspection regions FOV in order, at least one dummy inspection region DFOV is set between a target inspection region that is to be inspected and a previous inspection region that is already inspected when there is no previous inspection region that is adjacent to the target inspection region (step S210). When the second inspection region FOV2 is the target inspection region that is to be inspected after the first inspection region FOV1 is inspected, the second inspection region FOV2 is too far spaced apart from the first inspection region FOV1. Therefore, when the height displacement of the second inspection region FOV2 is estimated by the tendency information of the first inspection region FOV1, the reliability of the height displacement of the second inspection region FOV2 may be lowered. Therefore, the reliability of the height displacement of the second inspection region FOV2 may be enhanced by setting the first dummy inspection region DFOV1 between the first inspection region FOV1 and the second inspection region FOV2 to use height tendency information of the first dummy inspection region DFOV1. As described above, a second dummy inspection region DFOV2 may be set between the third inspection region FOV3 and the fourth inspection region FOV4, and a third dummy inspection region DFOV3 maybe set between the fifth inspection region FOV5 and the sixth inspection region FOV6.

Setting the dummy inspection region may be performed during setting inspection order of the inspection regions FOV or before inspecting the target inspection region FOV.

Then, the height displacement of the target inspection region FOV is estimated by using height tendency information of at least one of the dummy inspection region DFOV adjacent to the target inspection region FOV and the previous inspection region FOV (step S220).

In detail, in estimating the height displacement of the target inspection region FOV, the height displacement of the target inspection region may be estimated by using the tendency information of the dummy inspection region DFOV and the previous inspection region FOV through the extrapolation method. On the other hand, in estimating the height displacement of the target inspection region FOV, the interpolation method may be used.

For example, when the target inspection region is the fourth inspection region FOV4 in FIG. 10, there are the first, second and third inspection regions FOV1, FOV2 and FOV3 that are already inspected, and the first and second dummy inspection regions DFOV1 and DFOV2. Therefore, the geographical features of the fourth inspection region FOV4 are estimated by using the tendency information of the first, second and third inspection regions FOV1, FOV2 and FOV3, and the first and second dummy inspection regions DFOV1 and DFOV2 through extrapolation method, and the z-axis position of the inspecting module 120 may be calculated by the geographical features of the fourth inspection region FOV4. In this case, all of the first, second and third inspection regions FOV1, FOV2 and FOV 3, and the first and second dummy inspection regions DFOV1 and DFOV2 may be used for estimating the geographical features of the fourth inspection region FOV4. However, some of the first, second and third inspection regions FOV1, FOV2 and FOV3, and the first and second dummy inspection regions DFOV1 and DFOV2 may be selected to be used for estimating the geographical features of the fourth inspection region FOV4.

For an example, when the target inspection region FOV is in the same row as the dummy inspection region DFOV and the previous inspection region FOV along the lengthwise direction of the stage 140, the height displacement of the target inspection region FOV may be estimated by linear tendency information. That is, the height displacement of the target inspection region FOV is estimated by using tendency information of the dummy inspection region DFOV and the previous inspection regions FOV on the same row along the lengthwise direction of the stage 140. For example, the height displacement of the center of the target inspection region FOV is estimated by using the height information of the centers of at least two of the dummy inspection region DFOV and the previous inspection regions FOV on the same row along the lengthwise direction of the stage 140. For example, when the target inspection region FOV is the second inspection region FOV2, the height displacement of the second inspection region FOV2 is estimated by using the height tendency information of the first dummy inspection region DFOV1 and the first inspection region FOV1.

For another exemplary embodiment, when the dummy inspection region DFOV and the previous inspection regions FOV are on the same row and the previous row along the lengthwise direction of the stage 140, the height displacement of the target inspection region FOV is estimated by using a surface tendency information. That is, the height displacement of the target inspection region FOV is estimated by using at least three tendency information of the dummy inspection region and the previous inspection regions on the same row and the previous row along the lengthwise direction of the stage 140. For example, the height displacement of the center of the target inspection region FOV may be estimated by using height information of the center of at least three of the dummy inspection region and the previous inspection regions FOV on the same row and the previous row along the lengthwise direction of the stage 140. In this case, it is preferable to use the tendency information of the dummy inspection region and the previous inspection regions FOV that are adjacent to the target inspection region FOV. For example, when the target inspection region FOV is the fourth inspection region FOV4, the height displacement of the fourth inspection region FOV4 is estimated by using the height tendency information of the first inspection region FOV1, the first dummy inspection region DFOV1 and the second dummy inspection region DFOV2 that are adjacent to the fourth inspection region FOV4.

The height tendency information of the dummy inspection region DFOV and the previous inspection regions FOV, for example, may correspond to height tendency information of all regions of the dummy inspection region DFOV and the previous inspection regions FOV. In this case, the height tendency information of all regions may include shape information of not only the three dimensional shape information of the target object 152 but also surface height information of the substrate 150. Alternatively, the height tendency information may correspond to height data of a portion of the region or point in the dummy inspection region DFOV and the previous inspection regions FOV. For example, a surface equation of the inspection region may be obtained by using height information of at least one region of interest ROI in the dummy inspection region DFOV or the previous inspection region. For example, the surface equation is obtained by using height information of at least one of the region of interest ROI, a bottom surface of the region of interest and an extended region of interest, and then height of the center or the contour obtained by the surface equation may be used as a reference data for estimating the height displacement. The surface equation of the dummy inspection region DFOV and the previous inspection region FOV may be obtained by height information of at least three points in the dummy inspection region DFOV and the previous inspection region FOV.

After the height displacement of the target inspection region FOV is estimated, the height of the inspecting module 120 is adjusted based on the estimated height displacement of the target inspection region FOV (step S230). For example, adjusting the height of the inspecting module 120 may be performed based on the height displacement of the center of the target inspection region FOV. The height adjustment of the inspecting module 120 is described referring to FIG. 5. Therefore, any further explanation will be omitted.

Then, the target inspection region FOV is inspected by using the inspecting module 120 of which height is adjusted (step S240).

In order to increase height inspection range corresponding to a warpage of the substrate 150, the method described above may adopt the multi-wavelength inspection method. The multi-wavelength inspection method is explained referring to FIG. 6 and FIG. 7. Therefore, any further explanation will be omitted.

According to an exemplary embodiment of the present invention, the dummy inspection regions are set between the inspection regions when the inspection regions are widely spaced apart from each other, and the tendency information of the dummy inspection region and the previous inspection regions are used so that the height displacement of the target inspection region may be more precisely estimated.

FIG. 11 is a flow chart showing a method of inspecting a substrate according to still another exemplary embodiment of the present invention, FIG. 12 is a plan view showing a substrate fixed to a stage according to still another exemplary embodiment of the present invention, and FIG. 13 is a side view showing a substrate fixed to a stage according to still another exemplary embodiment of the present invention.

Referring to FIG. 1, FIG. 11, FIG. 12 and FIG. 13, according to still another exemplary embodiment of the present invention, at least one substrate 150 is mounted on the substrate transferor 160 and fixed by a stage 140. In other words, the substrate 150 is fixed by the stage 140 in a state of being mounted on the substrate transferor 160. In inspecting the substrate 150 having the plurality of inspection regions FOV which are divided and being mounted on the substrate transferor 160, an inspection order for the inspection regions FOV are set (step S300). For example, the inspection order may be set in a zigzag shape along a lengthwise direction of the stage 140.

Then, a first inspection region FOV1 is measured to acquire a height displacement ΔH of the substrate 150 with reference to a measuring reference surface H1 of the inspecting module 120 that is already set (step S310). In general, an initial z-axis height of the inspecting module 120 is set with reference to the substrate 150 having the target object 152 and fixed by the stage 140. For example, the initial z-axis height of the inspecting module 120 may be set with reference to a lower surface of the upper stage 144. That is, for a conventional case without the substrate transferor 160, when the substrate 150 is loaded, the lower stage 142 moves upward to fix the substrate 150 between the upper stage 144 and the lower stage 142. Therefore, the z-axis height of the camera 130 is adjusted with reference to an upper surface of the substrate 150 (or an initial z-axis reference surface of camera). However, when the substrate 150 is loaded together with the substrate transferor 160 such as a tray or a jig, the substrate transferor 160 induces height displacement ΔH. Therefore, it is required to adjust the z-axis height of the inspection module 120 even in the first inspection region FOV1.

For this, the height of the inspecting module 120 is adjusted with reference to the height displacement ΔH in the first inspection module (step S320). For example, the height of the inspecting module 120 is adjusted with reference to the height displacement ΔH of the initial z-axis height of the camera 130 and the first inspection region FOV1 that is measured. That is, the inspecting module 120 is moved along the z-axis by amount of the height displacement ΔH corresponding to the height difference between the upper surface of the substrate transferor 160 fixed by the stage 140 and the upper surface of the substrate 150 mounted on the substrate transferor 160.

Then, the first inspection region FOV1 is inspected by using the inspecting module 120 of which height is adjusted (step S330).

Then, the height displacement of the target inspection region that is to be inspected is estimated by using the tendency information regarding to at least one previous inspection region that is already inspected (step S340). This step S340 is explained referring to FIG. 2 or FIG. 10. Therefore, any further explanation will be omitted.

After the height displacement is estimated, the height of the inspecting module 120 is adjusted by using the estimated height displacement of the target inspection region (step S350). For example, the height adjustment of the inspecting module 120 is performed with reference to the height of the center of the target inspection region. The height adjustment of the inspecting module 120 is explained referring to FIG. 5. Therefore, any further explanation will be omitted.

Then, the target inspection region FOV is inspected by using the inspecting module 120 of which height is adjusted.

In order to increase height inspection range corresponding to a warpage of the substrate 150, the method described above may adopt the multi-wavelength inspection method. The multi-wavelength inspection method is explained referring to FIG. 6 and FIG. 7. Therefore, any further explanation will be omitted.

According to an exemplary embodiment, the z-axis height of the camera 130 is adjusted by an amount of height displacement ΔH of the camera 130, which is induced by the substrate transferor 160 such as a tray or a jig, when the substrate 150 is transferred by the substrate transferor 160, so that the reliability of the inspection may be more enhanced.

FIG. 14 is a flow chart showing a method of inspecting a substrate according to still another exemplary embodiment of the present invention.

Referring to FIG. 1, FIG. 5 and FIG. 14, in inspecting the substrate 150 having a plurality of inspection region FOV in order, it is checked if there is at least one previous inspection region FOV that is already inspected near a target inspection region FOV to be inspected (step S400).

When there is not the previous inspection region FOV near the target inspection region FOV, the inspecting module 120 is transferred along a z-axis to an initial position to adjust a focus (step S410). This step corresponds to an initial inspection of the target object 152 formed on the substrate 150. The z-axis initial position of the inspecting module 120 is set by the substrate 150 fixed by the stage 140. For example, the z-axis initial position of the inspecting module 120 corresponds to a data obtained by z-axis calibration of the inspecting module 120.

When there is the previous inspection region FOV near the target inspection region FOV, an z-axis position of the inspecting module 120 in the target inspection region is estimated by using tendency information of the previous inspection region (step S420).

In detail, estimation of the z-axis position of the inspecting module 120 in the target inspection region may be performed by two steps. First, the geographical features of the target inspection region FOV are estimated by tendency information of the previous inspection region FOV through the extrapolation method. Then, the z-axis position of the inspecting module 120 is adjusted by using the geographical features. Alternatively, in estimating the geographical features of the target inspection region FOV, not only the extrapolation method but also an interpolation method may be used.

The above step S420 will be explained using examples. When the target inspection region FOV is the fifth inspection region FOV5 in FIG. 5, there are the previous inspection regions of the first, the second, the third and the fourth inspections regions FOV1, FOV2, FOV3 and FOV4 near the fifth inspection region FOV5. Therefore, the geographical features of the fifth inspection region FOV5 is estimated by using the tendency information of the first through fourth inspection regions FOV1, FOV2, FOV3 and FOV4 through the extrapolation method, and then the z-axis position of the inspecting module 120 is calculated by the geographical features of the fifth inspection region FOV5. In this case, all geographical features of the first, second, third and fourth inspection regions FOV1, FOV2, FOV3 and FOV4 may be used, but at least one of the geographical features of the first, second, third and fourth inspection regions FOV1, FOV2, FOV3 and FOV4 may be used. That is, a step of selecting previous inspection regions for estimating the geographical features of the fifth inspection region FOV5 may be performed among the first, second, third and fourth inspection regions FOV1, FOV2, FOV3 and FOV4, before estimating the geographical feature of the fifth inspection region FOV5.

The extrapolation method of the step of estimating the z-axis position of the inspecting module 120 in the target inspection region (step S420) may correspond to a method of estimating the height in the target inspection region FOV by using the height information in the geographical features of the previous inspection region FOV. In this embodiment, the height information of the previous inspection region FOV may be height information of entire region of the previous inspection region FOV. However, the height information of the previous inspection region FOV may be height information of a portion or a point of the previous inspection region FOV. For example, the height of the target inspection region FOV may be estimated by a center point of the previous inspection region FOV or at least one point in a contour of the previous inspection region FOV. Here, the height of the previous inspection region FOV and the height of the target inspection region FOV may mean the height of the substrate in FIG. 5.

After estimating the z-axis position of the inspecting module 120, the inspecting module 120 is transferred to the estimated z-axis position along a z-axis to adjust focus (step S430). For example, when the geographical features of the fifth inspection region FOV5 is lower than the geographical features of the fourth inspection region FOV4, the inspecting module 120 is lowered along a z-axis. On the contrary, when the geographical features of the fifth inspection region FOV5 s higher than the geographical features of the fourth inspection region FOV4, the inspecting module 120 is raised along a z-axis.

After the step of initial focus adjustment (step S410) or the step of estimated focus adjustment (step S430), the inspecting module 120 or the stage 140 is transferred along the XY axis, and the target inspection region FOV is inspected (step S440). On the other hand, the XY axis transferring of the stage 140 is performed after the step of estimated focus adjustment (step S430) in the present embodiment. However, the XY axis transferring of the stage 140 may be performed before or during the step of estimated focus adjustment (step S430). Further, the method of inspecting a substrate may adopt a multi-wavelength inspection method for increasing a scope of height inspection corresponding to the warpage of the substrate 150. The multi-wavelength inspection method is explained referring to FIG. 6 and FIG. 7. Therefore, any further explanation will be omitted.

After the step of inspecting the target inspection region FOV, it is checked that all of the inspection regions FOV are inspected (step S450). When all of the inspection regions FOV are not inspected, an inspection step is increased to inspect a next target inspection region FOV (step S460). For example, when the substrate 150 is divided into nine inspection regions (FOV1~FOV9) and the inspection of the fifth inspection region FOV5 is completed, the inspection step is increased from five to six and inspection process for the sixth inspection region FOV6 is performed. However, when inspecting all of the inspection regions FOV is completed, inspection process is ended.

On the other hand, the above method of inspecting a substrate may optionally include a step of adjusting focus of the substrate-inspecting apparatus 100 by using a laser range finder (not shown). For example, when the difference between the estimated geometrical features of the target inspection region FOV and the real geometrical features of the target inspection region FOV is greater than error range so that the focusing is not good, focus readjusting of the substrate-inspecting apparatus 100 is preferable by using the laser range finder (not shown).

As described above, according to the present exemplary embodiment of the present invention, it is checked if there is at least one previous inspection region FOV that is already inspected near a target inspection region FOV to be inspected before inspecting the target inspection region FOV, and the focus of the substrate-inspecting apparatus is adjusted by using geographical features of the previous inspection regions when there is the previous inspection region FOV, so that the inspection time may be reduced. That is, according to a conventional inspection method, a step of measuring the distance between the camera 130 and the substrate 150 to adjust the focus of the substrate-inspecting apparatus 100 is required, but the step of measuring the distance between the camera 130 and the substrate 150 is not required to reduce the inspection time according to the method of the present invention.

FIG. 15 is a flow chart showing a method of inspecting a substrate according to still another exemplary embodiment of the present invention, and FIG. 16 is a plan view showing one inspection region.

Referring to FIG. 15 and FIG. 16, when a large sized substrate 150 is divided by a plurality of inspection regions FOV, a region of interest ROI, in which a target object 152 is disposed, may be too much to one side in the inspection region FOV as shown in FIG. 16. In inspecting the substrate 150, all regions in the inspection region FOV is not inspected. Instead, a region, in which the target object 152 is formed, is set as the region of interest ROI and only the region of interest ROI is inspected to reduce the amount of data and reduce inspection time. When the region of interest ROI is not disposed at a center portion of the inspection region FOV but too much to one side as shown in FIG. 16, a tendency information of entire inspection region FOV may not be obtained by only the data of the region of interest ROI.

Therefore, the present exemplary embodiment provides a method of inspecting a substrate, which is capable of obtaining relatively precise height tendency information of the inspection region FOV by setting a dummy region of interest DROI other than the region of interest ROI.

For this, a target region of interest ROI in which a target object 152 is formed and a dummy region of interest DROI are set in at least one inspection region FOV to acquire height tendency of a target inspection region FOV (step S500).

A region around the target object 152 that is to be inspected is set as the target region of interest ROI. The substrate-inspecting apparatus 100 automatically set the target region of interest ROI in an inspection region FOV according to the target object 152 by using information of the substrate 150, which include a position of the target object 152.

The dummy region of interest DROI is set aside from the target region of interest ROI in order to obtain the tendency information of the inspection region FOV. It is preferable to set a region, which is far from the target region of interest ROI, as the dummy region of interest DROI, in order to precisely estimate the height tendency of entire regions of the inspection region FOV. For example, when the target region of interest ROI is in the second quadrant of the inspection region FOV as shown in FIG. 16, the dummy region of interest DROI is set in the fourth quadrant of the inspection region FOV, which is diagonally disposed with respect to the second quadrant.

The dummy region of interest DROI may be set by a hand of an operator. That is, when an operator decide that the target region of interest ROI is not disposed at a center portion of the region of interest FOV, the operator may set the dummy region of interest DROI in the region of interest FOV aside from the target region of interest ROI. When the dummy region of interest DROI is set by the hand of the operator, the inspection module 120 performs data processing of the target region of interest ROI and the dummy region of interest DROI.

Alternatively, the region of interest may be automatically set based on a position of the target region of interest ROI. That is, after the position of the target region of interest ROI is checked, a region that is spaced apart from the target region of interest ROI may be automatically set as the dummy region of interest DROI.

Then, height displacement of a next inspection region FOV is estimated by using the height tendency obtained by at least one of the target region of interest ROI and the dummy region of interest DROI (step S510). For example, a surface equation of the inspection region FOV is obtained by using height information of at least one of region of interest ROI and the dummy region of interest DROI, and the surface equation may be used as the tendency information.

As described above, when the real region of interest ROI and the dummy region of interest DROI in the inspection region FOV are used for the tendency information, the tendency information may be more precisely estimated. Therefore, the height displacement of the next inspection region FOV can be more precisely estimated by using the tendency information.

Then, after estimating the height displacement of the next inspection region FOV, the height of the inspecting module is adjusted, based on the estimated height displacement (step S520). For example, when the next inspection region is fifth inspection region FOV5, a height of the center of the fifth inspection region FOV5 is compared with the height of the fourth inspection region FOV4 which is the previous inspection region. When the height of the fifth inspection region FOV5 is lower than the height of the fourth inspection region FOV4, the inspecting module 120 is lowered along a z-axis direction by amount of the height difference. When the height of the fifth inspection region FOV5 is higher than the height of the fourth inspection region FOV4, the inspecting module 120 is raised along a z-axis direction by amount of the height difference. In comparing the height displacement of the next inspection region FOV, the initial z-axis height which is already set may be compared with the next inspection region FOV, instead of the height of the previous inspection region. The initial z-axis height is set based on the height of the substrate 150 fixed by the stage 140. For example, the initial z-axis height may be obtained by z-axis calibration of the inspecting module 120. The height of the inspecting module 120 may be adjusted before the inspecting module 120 is transferred to the next inspection region FOV, after the inspecting module 120 is transferred to the next inspection region FOV, or during the inspecting module 120 is transferred to the next inspection region FOV.

Then, the next inspection region FOV is inspected by using the inspecting module of which height is adjusted (step S530).

According to the present invention, in inspecting the plurality of inspection region in order, the height of the inspecting module 120 is adjusted by using the tendency information of at least one surface height tendency information of the previous inspection region. Therefore, the focus of the inspecting module may be precisely adjusted.

Further, the surface height tendency information becomes more reliable since the surface height tendency information of the real region of interest ROI and the dummy region of interest DROI are used together.

In order to increase height inspection range corresponding to a warpage of the substrate 150, the method described above may adopt the multi-wavelength inspection method. The multi-wavelength inspection method is explained referring to FIG. 6 and FIG. 7. Therefore, any further explanation will be omitted.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A method of inspecting a substrate by using a substrate-inspecting apparatus having at least one projecting module projecting a patterned light onto a substrate fixed on a stage and an inspecting module with a camera capturing an image, and inspecting a plurality of inspection regions of the substrate step by step, the method comprising:
   setting an inspection order of the inspecting regions according to a lengthwise direction of the substrate;
   estimating height displacement of a target inspection region by using a height tendency information regarding at least one previous inspection region that is already inspected, the height tendency information including three dimensional shape information of an object of the at least one previous inspection region and surface height information of the substrate;
   adjusting height of the inspecting module by using the estimated height displacement of the target inspection region; and
   inspecting the target inspection region by using the inspecting module of which height is adjusted.

2. The method of claim 1, wherein the height displacement of a target inspection region is estimated by using the height tendency information of at least one previous inspection region that is already inspected through an extrapolation method.

3. The method of claim 1, wherein the height displacement of a target inspection region is estimated by using height information of at least two previous inspection regions existing in a same row along the lengthwise direction.

4. The method of claim 1, wherein the height displacement of a target inspection region is estimated by using height information of at least three previous inspection regions existing in a same row and a previous row along the lengthwise direction.

5. The method of claim 1, wherein the height of the inspecting module is adjusted based on height displacements of a center of the target inspection region and the previous inspection region.

6. The method of claim 1, wherein the projecting module comprises:
   at least one first projecting module projecting a first patterned light with a first wavelength; and
   at least one second projecting module projecting a second patterned light with a second wavelength that is different from the first wavelength.

7. The method of claim 1, wherein the projecting module projects a first patterned light with a first wavelength and a second patterned light with a second wavelength different from the first wavelength inسequence.

8. A method of inspecting a substrate by using a substrate-inspecting apparatus having at least one projecting module projecting a patterned light onto a substrate fixed on a stage and an inspecting module with a camera capturing an image, and inspecting a plurality of inspection regions of the substrate step by step, the method comprising:
setting an inspection order of the inspecting regions;
setting at least one dummy inspection region between a target inspection region and a previous inspection region that is already inspected, when there is no previous inspection region that is adjacent to the target inspection region;
estimating height displacement of a target inspection region by using a height tendency information regarding at least one of the dummy inspection region and the previous inspection region;
adjusting height of the inspecting module by using the estimated height displacement of the target inspection region; and
inspecting the target inspection region by using the inspecting module of which height is adjusted.

9. The method of claim 8, wherein the projecting module comprises:
at least one first projecting module projecting a first patterned light with a first wavelength; and
at least one second projecting module projecting a second patterned light with a second wavelength that is different from the first wavelength.

10. The method of claim 8, wherein the projecting module projects a first patterned light with a first wavelength and a second patterned light with a second wavelength different from the first wavelength in sequence.

11. A method of inspecting a substrate by using a substrate-inspecting apparatus having at least one projecting module projecting a patterned light onto a substrate mounted on a substrate transferor and fixed to a stage together with the substrate transferor and an inspecting module with a camera capturing an image, and inspecting a plurality of inspection regions of the substrate step by step, the method comprising:
setting an inspection order of the inspecting regions according to a lengthwise direction of the substrate;
measuring a first inspection region to acquire a height displacement of the first inspection region with reference to a measuring reference surface of the inspecting module, which is already set;
adjusting height of the inspecting module by using the height displacement; and
inspecting the first inspection region by using the inspecting module of which height is adjusted,
wherein the method further comprises:
estimating height displacement of a target inspection region to be inspected next by using a height tendency information regarding at least one previous inspection region that is already inspected;
adjusting height of the inspecting module by using the estimated height displacement of the target inspection region; and
inspecting the target inspection region by using the inspecting module of which height is adjusted.

12. The method of claim 11, wherein the projecting module comprises:
at least one first projecting module projecting a first patterned light with a first wavelength; and
at least one second projecting module projecting a second patterned light with a second wavelength that is different from the first wavelength.

13. The method of claim 11, wherein the projecting module projects a first patterned light with a first wavelength and a second patterned light with a second wavelength different from the first wavelength in sequence.

14. A method of inspecting a substrate by using a substrate-inspecting apparatus having at least one projecting module projecting a patterned light onto a substrate fixed on a stage and an inspecting module with a camera capturing an image, and inspecting a plurality of inspection regions of the substrate step by step, the method comprising:
checking if there is at least one previous inspection region that is already inspected near a target inspection region to be inspected;
transferring the inspecting module to an initial position along a z-axis, when there is not the previous inspection region;
estimating a z-axis position of the inspecting module in the target inspection region by using height tendency information of the previous inspection region, when there is the previous inspection region;
transferring the inspecting module to the estimated z-axis position along a z-axis; and
inspecting the target inspection region by using the inspecting module.

15. The method of claim 14, wherein the projecting module comprises:
at least one first projecting module projecting a first patterned light with a first wavelength; and
at least one second projecting module projecting a second patterned light with a second wavelength that is different from the first wavelength.

16. The method of claim 14, wherein the projecting module projects a first patterned light with a first wavelength and a second patterned light with a second wavelength different from the first wavelength in sequence.

17. A method of inspecting a substrate by using a substrate-inspecting apparatus having at least one projecting module projecting a patterned light onto a substrate fixed on a stage and an inspecting module with a camera capturing an image, and inspecting a plurality of inspection regions of the substrate step by step, the method comprising:
setting a dummy region of interest for acquiring height tendency of a target inspection region, and a real region of interest on which a target object is formed, at a location that is apart from the target region of interest;
estimating height displacement of a next inspection region by using the height tendency obtained by at least one of the real region of interest and the dummy region of interest;
adjusting height of the inspecting module based on the estimated height displacement; and
inspecting the next inspection region by using the inspecting module of which height is adjusted.

18. The method of claim 17, wherein the dummy region of interest is set by a hand of an operator.

19. The method of claim 17, wherein the dummy region of interest is automatically set based on a position of the real region of interest.

20. The method of claim 19, wherein the dummy region of interest is automatically set by:
checking a position of the real region of interest in the inspection region; and
setting the dummy region of interest as a region of interest at a greatest distance from the real region of interest.

21. The method of claim 17, wherein the projecting module comprises:
- at least one first projecting module projecting a first patterned light with a first wavelength; and
- at least one second projecting module projecting a second patterned light with a second wavelength that is different from the first wavelength.

22. The method of claim 17, wherein the projecting module projects a first patterned light with a first wavelength and a second patterned light with a second wavelength different from the first wavelength in sequence.

* * * * *